United States Patent [19]

Wehner et al.

[11] 4,339,383

[45] Jul. 13, 1982

[54] IMIDE CONTAINING STABILIZERS FOR CHLORINATED THERMOPLASTICS

[75] Inventors: Wolfgang Wehner, Zwingenberg; Klaus-Peter Michaelis, Lindenfels/Odenwald; Rainer Schneider, Bensheim-Auerbach, all of Fed. Rep. of Germany

[73] Assignee: Ciba-Geigy Corporation, Ardsley, N.Y.

[21] Appl. No.: 165,304

[22] Filed: Jul. 2, 1980

[30] Foreign Application Priority Data

Nov. 7, 1979 [CH] Switzerland .......................... 6477/79

[51] Int. Cl.³ .................. C07D 487/04; C07D 403/12; C07D 403/06; C07D 209/48
[52] U.S. Cl. .................... 548/419; 544/22 D; 544/221; 544/223; 544/219; 560/51; 560/174; 560/178; 548/318; 548/304; 544/204; 544/196; 548/429; 548/431; 548/433; 548/434; 548/461; 548/479; 548/513; 548/520; 548/547; 524/89; 524/94
[58] Field of Search ........... 260/326 A, 326 S, 326 N, 260/326 C

[56] References Cited

U.S. PATENT DOCUMENTS 3,346,536 10/1967 Kauder et al. .................... 260/45.85
4,145,556 3/1977 Hiraih et al. ........................ 560/75
4,174,455 12/1978 Habermeir et al. ................. 560/49

FOREIGN PATENT DOCUMENTS 1095677 12/1967 United Kingdom ........... 260/326 A

OTHER PUBLICATIONS

Chem. Abstracts Subject Index (1967–1971), Entry No. 73:P36471q.

Primary Examiner—Mark L. Berch
Attorney, Agent, or Firm—Harry Falber

[57] ABSTRACT

The invention relates to alkanolamido-β-carboxylic acid esters of the formula I

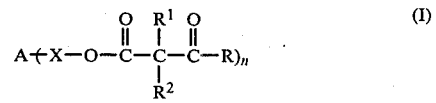

A full definition of the above formula will be found in claim 1 of the specification. These compounds are useful stabilizers for chlorinated thermoplastics.

3 Claims, No Drawings

IMIDE CONTAINING STABILIZERS FOR CHLORINATED THERMOPLASTICS

The present invention relates to novel alkanolamido-β-ketonic acid esters and their use by themselves or with other stabilisers for stabilising chlorinated thermoplastics.

Nitrogen-free acetoacetates are known from German Offenlegungsschrift No. 1 569 407 as non-toxic heat co-stabilisers for polyvinyl chloride resins which are intended in particular for use in food packaging. It has been demonstrated, however, that the stabilising action of these compounds is not entirely satisfactory in actual practice.

It has now been found that alkanolamido-β-ketonic acid esters ensure a surprisingly good stabilisation of chlorinated thermoplastics that also satisfies the requirements of practice.

Accordingly, the present invention provides compounds of the formula I

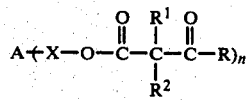

(I)

wherein n is an integer from 1 to 3, R is $C_1-C_{24}$alkyl or phenyl, each of $R^1$ and $R^2$ independently is hydrogen or R, and X is $C_1-C_6$alkylene which can be interrupted by —O—, and, if n is 1, A is one of the groups of the formulae

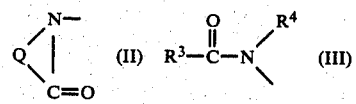

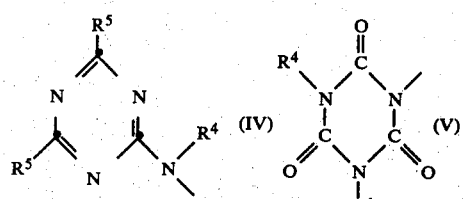

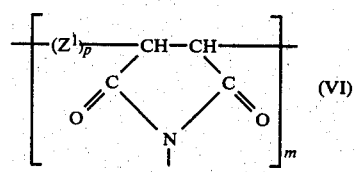

wherein p is 0 or 1 and m is an integer from 1 to 250, $Z^1$ is ethylene which can be substituted by $C_1-C_{24}$alkyl or $C_1-C_{24}$ alkoxy, $C_2-C_{24}$alkenyl, phenyl, $C_2-C_{24}$carbalkoxy, carbophenoxy, $C_2-C_{24}$alkanoyloxy, benzoyloxy, halogen or cyano, $R^3$ is hydrogen, $C_1-C_{24}$alkyl which can be substituted by halogen atoms, $C_6-C_{14}$aryl or $C_7-C_{16}$aralkyl, each of which can be substituted by —OH, —$NH_2$ or $C_1-C_4$alkyl, $R^4$ is hydrogen, $C_1-C_{24}$alkyl, a group —X—OH or —X—OCO—$CH_2$—CO—R, and $R^5$ is hydrogen, —OH, —$OR^3$, —$SR^3$, —$R^3$, —$NHR^3$ or —X—OH, Q is a group —Z—CO, wherein the carbonyl group is attached to the nitrogen of the formula II, and Z is ethylene which can be added to a 1,3-homodiene or (oxa- or aza-) heterodiene, which in turn can be the constituent, or partial constituent, of a homocyclic or (oxa-, thia- or aza-) heterocyclic ring system containing 5 to 40 ring members and 1 to 10 rings, or Z is vinylene, o-phenylene which can be substituted by a group —CON($R^6$)$R^7$, —COO$R^8$ or —COS$R^8$, or by 4 halogen atoms, or is the group —$CH_2$—S—$CH_2$—, $R^6$ and $R^7$ are the same or different and are hydrogen or $C_1-C_{12}$-alkyl, and $R^8$ is $C_1-C_{12}$alkyl or a group —$CH_2$—COO$R^9$, wherein $R^9$ is $C_1-C_{12}$alkyl, or Q is a group which completes a 5- to 10-membered heterocyclic ring system containing at least 2 heteroatoms, and, if n is 2, A is one of the groups of the formulae

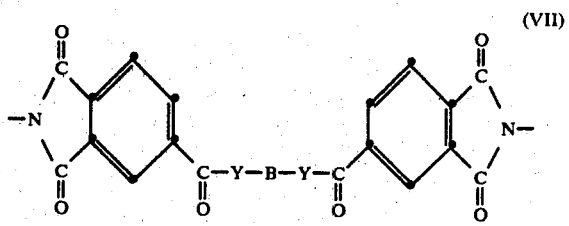

(VII)

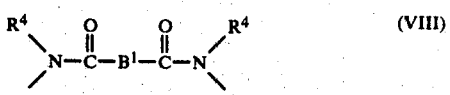

(VIII)

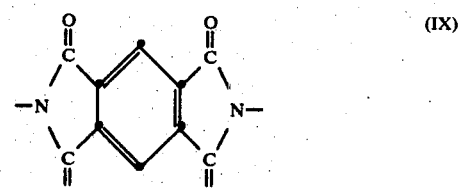

(IX)

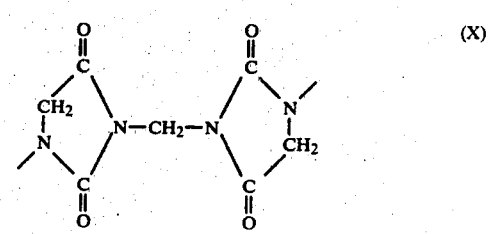

(X)

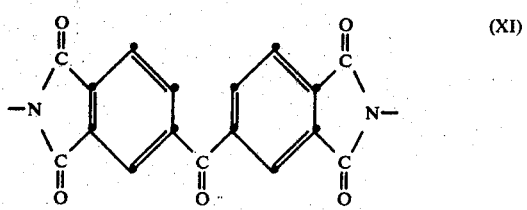

(XI)

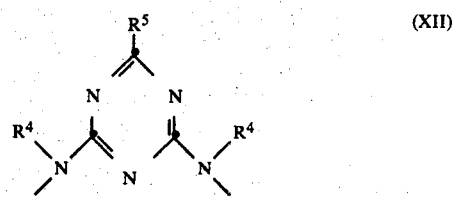

(XII)

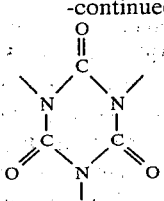
(XIII)

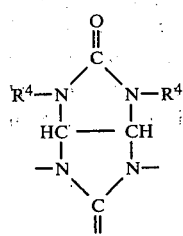
(XIV)

wherein Y can be —O— or —NH—, B is $C_1$–$C_6$alkylene, p-phenylene or one of the groups —[(CH$_2$)$_q$O]$_r$(CH$_2$)$_q$— or —[(CH$_2$)$_q$S]$_r$(CH$_2$)$_q$—, wherein q is an integer from 1 to 4 and r is an integer from 1 to 3, and $B^1$ is a direct bond or has the same meaning as B, or is $C_{10}$–$C_{14}$arylene or $C_5$–$C_8$cycloalkylene, and, if n is 3, A is a group of the formula

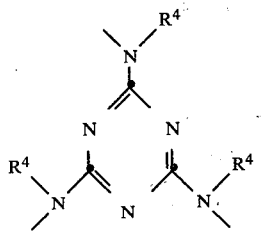
(XV)

wherein $R^4$ is as defined above.

$C_1$–$C_{12}$Alkyl can be branched or unbranched alkyl, e.g. methyl, ethyl, n-propyl, isopropyl, n-butyl, tert-butyl, n-pentyl, 2-methylpentyl, hexyl, 2,4-dimethylpentyl, octyl, 6-methylheptyl, 2-ethylhexyl, decyl or dodecyl.

$C_1$–$C_{24}$Alkyl can be e.g. the groups specified above for $C_1$–$C_{12}$alkyl and, in addition, e.g. branched or unbranched tridecyl, tetradecyl, hexadecyl, octadecyl, eicosyl, docosyl, tricosyl or tetracosyl.

$C_1$–$C_6$Alkylene is branched or, in particular, straight-chain alkylene, e.g. methylene, ethylene, trimethylene, tetramethylene, pentamethylene or hexamethylene. Preferred alkylene groups are methylene and especially ethylene and trimethylene.

$C_1$–$C_{24}$Alkoxy is e.g. methoxy, ethoxy, n-propoxy, isopropoxy, n-butoxy, tert-butoxy, n-pentoxy, n-hexyloxy, 2,4-dimethylpentyloxy, n-octyloxy, 2-ethylhexyloxy, or is branched or unbranched decyloxy, dodecyloxy, tridecyloxy, tetradecyloxy, hexadecylocy, octadecyloxy, eicosyloxy, docosyloxy, tricosyloxy or tetracosyloxy, with methoxy and ethoxy being preferred.

$C_2$–$C_{24}$Alkenyl is e.g. vinyl, allyl, methallyl or branched or unbranched 2-butenyl, 2-hexenyl, 3-hexenyl, 2-octenyl, 2-dodecenyl, 3-dodecenyl, 2-tetradecenyl, 2-hexadecenyl or 2-octydecenyl. Allyl is preferred.

$C_2$–$C_{24}$Carboalkoxy is in particular carbomethoxy, carboethoxy, carbopropoxy, carbobutoxy. $C_2$–$C_{24}$Alkanoyloxy is preferably acetyloxy.

Halogen is preferably bromine or, most preferably chlorine.

$B^1$ as $C_{10}$–$C_{14}$arylene is e.g. 2,3- or 1,8-naphthylene or 2,3-anthracenylene. $B^1$ as $C_5$–$C_8$cycloalkylene is in particular hexylene.

Where Z is ethylene which can be added to a 1,3-homodiene or (oxa- or aza) heterodiene, which in turn can be a constituent, or partial constituent, of a homocyclic or (oxa-, thia- or aza) heterocyclic ring system containing 5 to 40 ring members and 1 to 10 rings, then A is e.g. one of the radicals of the formulae

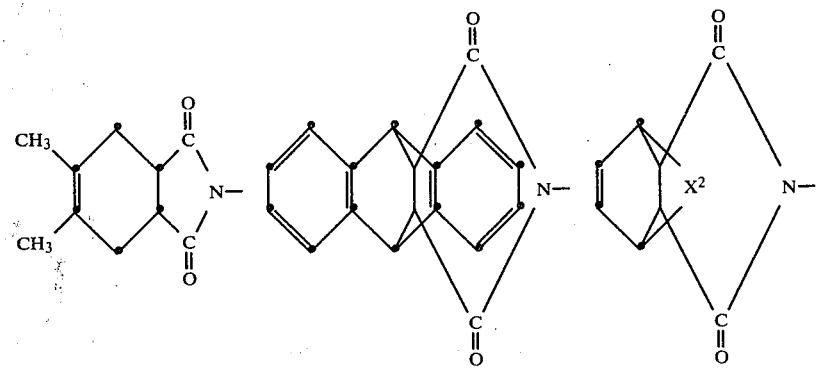

wherein $X^2$ is —O—, —S—, —N($R^1$)($R^2$)— or —C($R^1$)($R^2$)—.

If Q is a group which completes a 5- to 10-membered heterocyclic ring system containing at least 2 heteroatoms, then A is e.g. a radical of one of the formulae

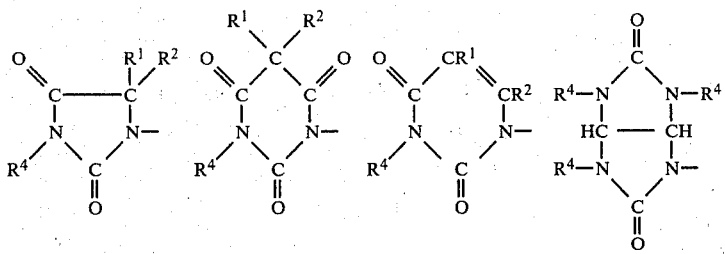

in which case Q is respectively a group —C(R¹)(R²)—CO—N(R⁴)—, —CO—C(R¹)(R²)—CO—N(R⁴)—, —CR¹=CR²—CO—N(R⁴)— or

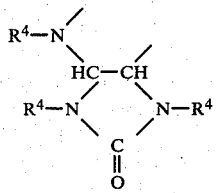

wherein each nitrogen is attached to the carbonyl group of the formula II.

$R^3$ as $C_6$-$C_{14}$aryl which can be substituted by —OH, —$NH_2$ or $C_1$-$C_4$alkyl is preferably phenyl which can be mono-, di- or trisubstituted, and is especially phenyl, 3,5-dimethyl-4-hydroxyphenyl or 3,5-di-tert-butyl-4-hydroxyphenyl.

$R^3$ as $C_7$-$C_{16}$aralkyl which can be substituted by —OH, —$NH_2$ or $C_1$-$C_4$alkyl is preferably benzyl or phenethyl which can be mono-, di- or trisubstituted, and is especially 3,5-dimethyl-4-hydroxybenzyl, 3,5-di-tert-butyl-4-hydroxybenzyl, 2-(3,5-dimethyl-4-hydroxyphenyl)ethyl or 2-(3,5-di-tert-butyl-4-hydroxyphenyl)ethyl.

Especially interesting compounds are those of the formula I wherein n is 1 or 2, R is methyl or phenyl, $R^1$ and $R^2$ are hydrogen, and X is $C_2$-$C_3$alkylene or a group —$CH_2CH_2O$—$CH_2CH_2$—, and, if n is 1, A is one of the groups of the formulae II, III, IV or V, wherein $R^3$ is $C_1$-$C_{24}$alkyl, $R^4$ is a group —X—OCO—$CH_2$—CO—R, wherein X and R have the preferred meanings given above, and $R^5$ is $C_1$-$C_4$alkoxy, and, if n is 2, A is one of the groups of the formulae VIII, IX, XI or XIV, wherein $B^1$ is a p-phenylene group and $R^4$ is hydrogen or the group —X—OCO—$CH_2$—CO—R, wherein X and R have the preferred meanings given above.

Preferred compounds are those of the formula I wherein R is methyl and X is $C_2$-$C_3$alkylene, n is 1 or 2, and, if n is 1, A is a group of the formula

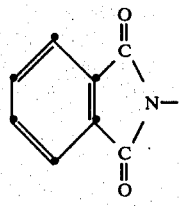

and, if n is 2, A is one of the groups of the formulae VIII, IX, XI or XIV, wherein B' is a p-phenylene group and $R^4$ is hydrogen or the group —X—OCO—CH₂—CO—R, wherein X and R have the preferred meanings given above.

The compounds of the formula I of this invention are obtained very smoothly in analogy to generally known transesterification reactions by reacting a β-ketonic acid ester of the formula XVI $$R-\overset{O}{\underset{}{C}}-\overset{R_1}{\underset{R_2}{C}}-\overset{O}{\underset{}{C}}-OR^{10} \qquad (XVI)$$

with an alkanolamide of the formula XVII $$A\ (\!X\!-\!OH)_n \qquad (XVII)$$

wherein n, A, R, $R^1$ and $R^2$ are as defined above and $R^{10}$ is methyl or ethyl.

It is advantageous to carry out this transesterification using a distillation column, as the methanol or ethanol formed during the reaction can be most easily separated therewith. The temperature for the transesterification is in the range from 50° to 200° C., preferably from 120° to 160° C.

If it is desired to effect total transesterification, then it is advantageous to use about twice the stoichiometric amount of methyl acetoacetate. Under stoichiometric conditions, only a partial reaction results. The reaction products obtained, however, are also useful stabilisers.

The alkanolamides employed as starting materials for the production of the stabilisers of this invention are known per se. If some of these compounds are new, they can be obtained by methods analogous to known ones, e.g.:

(a) from a carboxylic anhydride and an alkanolamine, e.g. in accordance with the equation

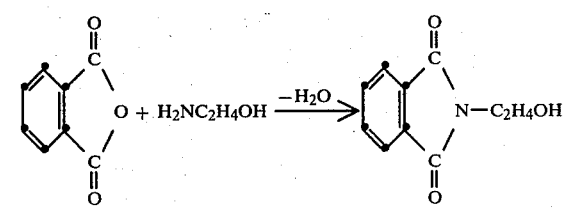

(b) from a carboxylic acid ester and a mono- or dialkanolamine, e.g. in accordance with the equations

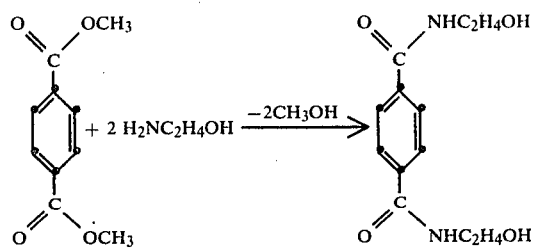

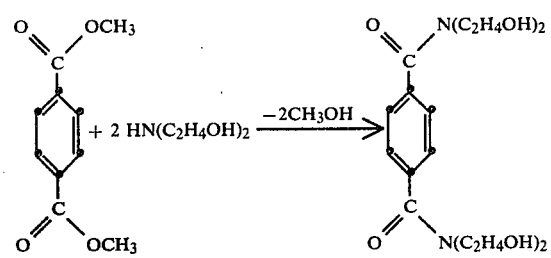

(c) from cyanuric chloride and a mono- or dialkanolamine, e.g. in accordance with the equations

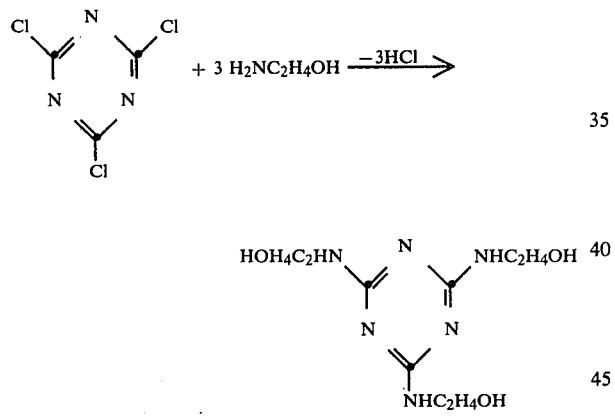

(d) from cyanuric acid and ethylene oxide, in accordance with the equation

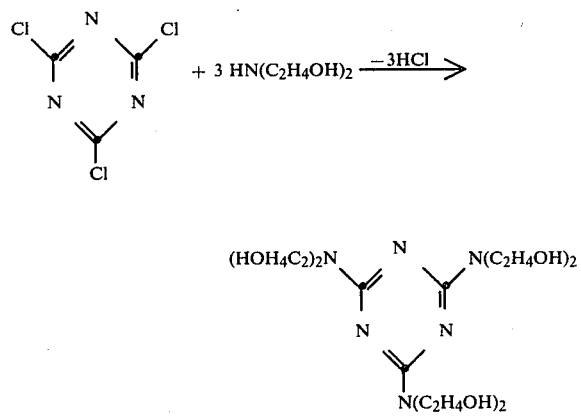

(e) from an imide and ethylene oxide or formaldehyde, e.g. in accordance with the equations

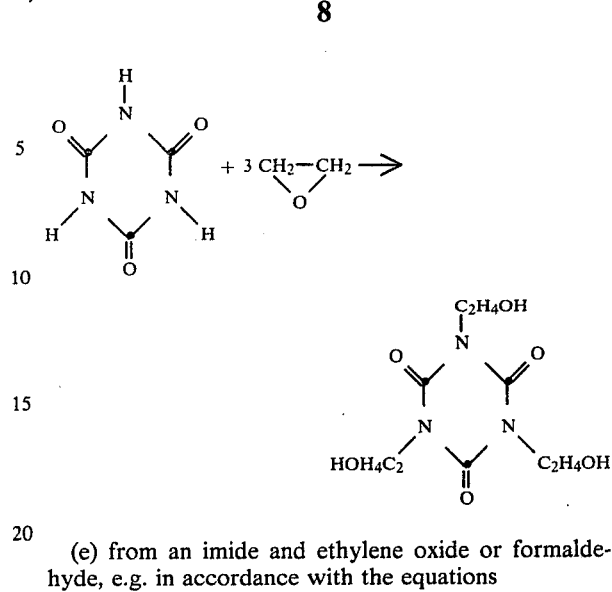

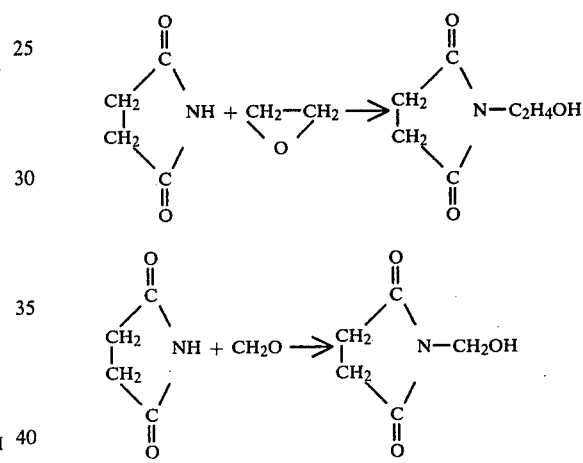

The β-ketonic acid esters of the formula XVI are known compounds.

The alkanolamido-β-ketonic acid esters of this invention are very suitable for protecting chlorinated thermoplastics against heat-induced degradation. They can be incorporated individually or in admixture with one another in the thermoplastics which it is desired to stabilise, before stabilising, in conventional apparatus and in respective amounts of 0.05 to 5.0% by weight, preferably 0.1 to 1.5% by weight, based on the entire composition.

Accordingly, it is also an object of the invention to provide stabilised compositions containing a chlorinated polymer and, as stabiliser, a compound of the formula I, or a mixture of compounds of the formula I, preferably together with other stabilisers.

Examples of chlorinated thermoplastics are polyvinylidene chloride and preferably polymers of, or based on, vinyl chloride. Suspension and mass polymers, and emulsion polymers having a low content of emulsifier, are preferred. Polyvinyl chloride can be plasticised or rigid polyvinyl chloride.

Examples of comonomers for thermoplastics based on vinyl chloride are: vinylidene chloride, trans-dichloroethane, ethylene, propylene, butylene, maleic acid, acrylic acid, fumaric acid or itaconic acid.

Depending on the end use, further additives can be incorporated in the moulding compound before, during or after the addition of the stabiliser mixture of the invention.

Examples of further additives with which the stabilisers of the invention can be used, are: antioxidants, such as 2,6-dialkylphenols, derivatives of alkylated hydroquinones, hydroxylated thiodiphenyl ethers, alkylidene bisphenols, O-, N- and S-benzyl compounds, hydroxybenzylated malonates, hydroxybenzyl aromatics, s-triazine compounds, amides of β-(3,5-di-tert-butyl-4-hydroxyphenyl)propionic acid, esters of β-(3,5-di-tert-butyl-4-hydroxyphenyl) propionic acid, esters of β-(5-tert-butyl-4-hydroxy-3-methylphenyl)propionic acid, esters of 3,5-di-tert-butyl-4-hydroxyphenylacetic acid, acylaminophenols, benzylphosphonates, aminoaryl derivatives, UV absorbers and light stabilisers, such as 2-(2'-hydroxyphenyl)benztriazoles, 2,4-bis-(2'hydroxyphenyl)-6-alkyl-s-triazines, 2-hydroxybenzophenones, 1,3-bis-2-(2'-hydroxybenzoyl)benzenes, esters of substituted or unsubstituted benzoic acids, acrylates, nickel compounds, sterically hindered amines, oxalic acid diamides, metal deactivators, phosphites, compounds which decompose peroxide, polyamide stabilisers, basic co-stabilisers, PVC stabilisers, nucleination agents or other additives, for example plasticisers, lubricants, emulsifiers, fillers, carbon black, asbestos, kaolin, talc, glass fibers, pigments, fluorescent whitening agents, flame retardants, antistatic agents.

Examples of further additives with which the stabilisers of the present invention can be used are listed on pages 18–24 of German Offenlegungsschrift No. 2 427 853.

Preferred co-stabilisers are calcium/zinc carboxylates and phosphites, e.g. trialkylphosphites, triarylphosphites, trialkarylphosphites or mixed alkyl/aryl phosphites.

The invention is illustrated in more detail by the following Examples, in which parts and percentages are by weight.

PREPARATORY EXAMPLES

EXAMPLE 1

With stirring, 46.5 g (0.2 mole) of adipic acid bis-ethanolamide and 93 g (0.8 mole) of methyl acetoacetate are heated together under transesterification conditions for 3 hours at 150° C. Methanol formed during the reaction is distilled off and then excess acetoacetate is removed in vacuo. The residue is recrystallised from acetone with the addition of activated carbon, affording 58.1 g (73% of theory) of adipic acid bis-2-ethanolamidoacetoacetate with a melting point of 98°–100° C.

$$O=C-NHC_2H_4OCOCH_2COCH_3$$
$$|$$
$$(CH_2)_4$$
$$|$$
$$O=C-NHC_2H_4OCOCH_2COCH_3$$

(stabiliser 1)

| Analysis: | C | H | N |
|---|---|---|---|
| calc.: | 54.0 | 7.1 | 7.0 |
| found: | 53.5 | 7.1 | 7.3 |

EXAMPLE 2

The procedure of Example 1 is repeated, replacing adipic acid bis-ethanolamide by the equivalent amount of succinic acid bis-ethanolamide. After recrystallisation, succinic acid bis-2-ethanolamido-acetoacetate with a melting point of 108°–110° C. is obtained in a yield of 51.0 g (69% of theory).

$$O=C-NHC_2H_4OCOCH_2COCH_3$$
$$|$$
$$(CH_2)_2$$
$$|$$
$$O=C-NHC_2H_4OCOCH_2COCH_3$$

(stabiliser 2)

| Analysis: | C | H | N |
|---|---|---|---|
| calc.: | 51.6 | 6.5 | 7.5 |
| found: | 51.0 | 6.5 | 7.8 |

EXAMPLE 3

The procedure of Example 1 is repeated, replacing adipic acid bis-ethanolamide by the equivalent amount of oxalic acid bis-ethanolamide. After recrystallisation, oxalic acid bis-2-ethanolamideo-acetoacetate with a melting point of 114°–116° C. is obtained in a yield of 45.2 g (68% of theory).

(stabiliser 3)

O=C-NHC_2H_4OCOCH_2COCH_3
|
O=C-NHC_2H_4OCOCH_2COCH_3

| Analysis: | C | H | N |
|---|---|---|---|
| calc.: | 48.8 | 5.9 | 8.1 |
| found: | 48.8 | 5.8 | 8.2 |

EXAMPLE 4

The procedure of Example 1 is repeated, replacing adipic acid bis-ethanolamide by the equivalent amount of terephthalic acid bis-2-ethanolamide. Yield: 69.6 g (83% of theory) of terephthalic acid bis-2-ethanolamido-acetoacetate with a melting point of 145° C.

(stabiliser 4)

| Analysis: | C | H | N |
|---|---|---|---|
| calc.: | 57.14 | 5.71 | 6.66 |
| found: | 59.2 | 6.6 | 6.4 |

The bis-ethanolamides used as starting materials in the foregoing Examples can be obtained by known methods from the corresponding diethyl carboxylates by reaction with ethanolamine, for example as described hereinbelow for succinic acid bis-ethanolamide: With stirring, 62.2 g (0.357 mole) of diethyl succinate and 48 g (0.785 mole) of ethanolamine are heated together for 3 hours at 130°–140° C. Methanol which has formed during the reaction is distilled off and then the residue which solidifies at 110° C., is digested in acetone, filtered, and collected by suction. The crude product is recrystallised from absolute ethanol, affording 69 g (95%) of a colourless powder with a melting point of 155°–157° C.

| Analysis: | C | H | N |
|---|---|---|---|
| calc.: | 47.0 | 7.9 | 13.7 |
| found: | 46.7 | 7.7 | 13.7 |

EXAMPLE 5

With stirring, 148.1 g (1 mole) of phthalic anhydride are added to 67.2 g (1.1 moles) of ethanolamine (exothermic reaction, internal temperature ~100° C.). The reaction mixture is stirred for 2 hours at a bath temperature of 140° C. (internal temperature ~120° C.) and then water and excess ethanolamine are stripped off in vacuo in the course of 20 minutes. Then 500 g of methyl acetoacetate (4.2 moles) are added and methanol which forms is distilled off under a weak vacuum (120–150 torr) in the course of 2 hours and at a bath temperature of 120° C. Excess acetoacetate is then stripped off in vacuo at a bath temperature of 120° C. in the course of 2 hours. The residue is recrystallised from a small amount of cold methanol, collected by filtration and dried, affording 209 g (76% of theory) of 1-(acetoacetyloxy-2-ethyl)phthalimide in the form of a pale yellow powder with a melting point of 83°–87° C.

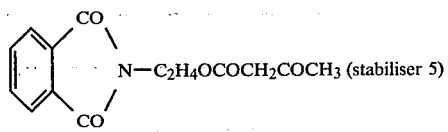

EXAMPLE 6

With stirring, 218 g (1 mole) of pyromellitic dianhydride are added in small portions to a solution of 122 g (2 moles) of ethanolamine in 300 ml of dimethyl formamide (exothermic reaction with black colouration). The reaction mixture is then refluxed (142° C.) and about 80 ml of a mixture of dimethyl formamide/water are distilled off until the boiling temperature of the dimethyl formamide is constant (153° C.). After cooling, the crystalline precipitate is collected by filtration and refluxed with 300 ml of methyl acetoacetate in a transesterification cooler until the methanol which has formed is distilled off. Excess acetoacetate is then stripped off. Repeated recrystallisation from acetone yields 384 g (80% of theory) of pure bis-N-(acetoacetyloxy-2-ethyl)pyromellitic diimide with a melting point of 161°–163° C.

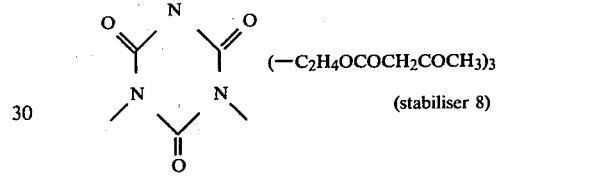

| Analysis: | C | H | N |
|---|---|---|---|
| calc.: | 55.93 | 4.27 | 5.93 |
| found: | 56.02 | 4.33 | 6.0 |

EXAMPLE 7

The procedure of Example 6 is repeated, replacing ethanolamine by the equivalent amount of 3-amino-1-propanol. Yield: 429.0 g (86% of theory) of pure bis-N-(acetoacetyloxy-3-propyl)pyromellitic diimide with a melting point of 115°–117° C.

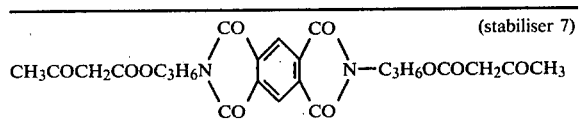

| Analysis: | C | H | N |
|---|---|---|---|
| calc.: | 57.54 | 4.79 | 5.59 |
| found: | 57.73 | 4.81 | 5.63 |

EXAMPLE 8

The procedure of Example 1 is repeated, replacing adipic acid bis-ethanolamide by the equivalent amount of trihydroxyethyl isocyanurate. After stripping off the volatile constituents in vacuo, isocyanuric acid tri-N-(2-ethylacetoacetate) is obtained in a yield of 60.0 g (86% of theory) in the form of a viscous substance with a refractive index of $n_D^{20}$: 1 4991.

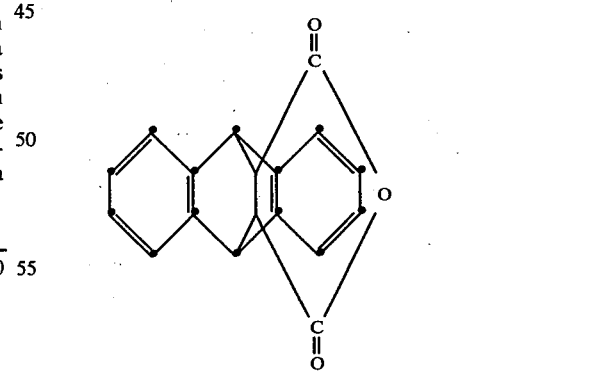

1,1-Methylene-bis-[3-(hydroxyethyl)-5,5-dimethyl hydantoin] can be reacted in analogous manner.

EXAMPLE 9

(a) With stirring, 178 g (1 mole) of anthracene are added in portions to a solution of 98 g (1 mole) of maleic anhydride in 200 ml of xylene. The mixture is then refluxed for 2 hours. After cooling, the residue is filtered with suction, affording 257 g of anhydride of the formula in the form of a white powder with a melting point of 263°–267° C.

(b) With stirring, a solution of 9.2 g (0.15 mole) of ethanolamine in 20 ml of chloroform is added dropwise to a solution of 41.1 g (0.15 mole) of the anhydride obtained in (a) in 100 ml of chloroform. The reaction is exothermic and a precipitate forms. Excess toluene is added and the batch is boiled for 5 hours in a transesterification cooler until the water that has formed is stripped off. The residue is filtered with suction, washed with chloroform, and dried, affording 46.4 g of ethanolamide of the formula

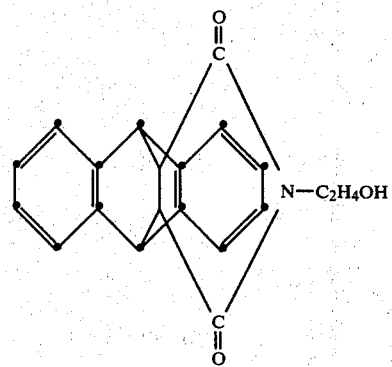

in the form of a colourless powder with a melting point of 216°–218° C.

(c) With stirring, 31.7 g (0.1 mole) of the ethanolamide obtained in (b), 23.2 g (0.2 mole) of methyl acetoacetate and 0.5 ml of tetrabutyl titanate are heated together to 160° C. for 15 hours in a transesterification cooler, during which time the methanol that forms is stripped off. The dark residue is dissolved in acetone, treated with activated carbon and collected by filtration. The solution is concentrated until a yellow, tacky residue remains. This residue is digested in diisopropyl ether, filtered with suction an dried, affording 30 g (75% of theory) of the ethanolamido-acetoacetate of the formula

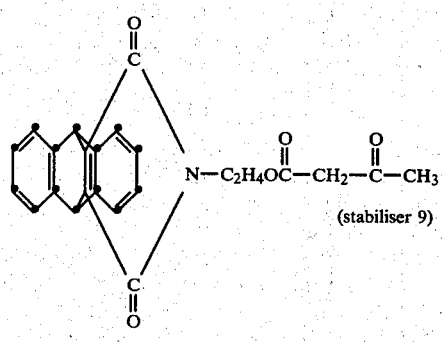

(stabiliser 9)

in the form of a colourless crystals with a melting point of 128°–130° C.

EXAMPLE 10

(a) With stirring, 12.3 g (0.2 mole) of ethanolamine are added dropwise to a ready prepared mixture of 38.4 g (0.2 mole) of trimellitic anhydride in 200 ml of toluene, while keeping the temperature at a maximum of 45° C. by ice-cooling. When the addition is complete, the mixture is refluxed and the water of reaction is removed as an azeotrope. The volatile constituents are stripped off and the batch is taken up in a small amount of ethanol and the solution is cooled. The precipitate is filtered with suction and dried, affording 53 g (82% of theory) of colourless 1-(2-hydroxyethyl)-4-hydroxycarbonylphthalimide with a melting point of 197°–198° C.

(b) 35.3 g (0.15 mole) of 1-(2-hydroxyethyl)-4-hydroxycarbonylphthalimide obtained in (a) are suspended in 250 ml of methanol. Under reflux, HCl gas is then introduced until saturation is reached. The clear solution obtained is slightly concentrated and cooled, whereupon a precipitate forms. This product is collected and dried, affording 35.2 g (94% theory) of 1-(2-hydroxyethyl)-4-methoxycarbonylphthalimide with a melting point of 81°–82° C. Transesterification with stearyl alcohol affords the corresponding stearyl product in quantitative yield. The corresponding acetoacetate is obtained by transesterification with ethyl acetoacetate.

(c) 24.9 g (0.1 mole) of 1-(2-hydroxyethyl)-4-methoxycarbonylphthalimide obtained in (b) are dissolved in 100 ml of methyl acetoacetate. The transesterification is complete after heating for 2 hours to 145° C. The volatile constituents are stripped off in vacuo, affording 30 g (90% of theory) of 1-(acetoacetyloxy-2-ethyl)-methoxycarbonylphthalimide in the form of an almost colourless viscous oil.

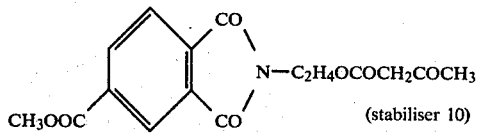

(stabiliser 10)

Transesterification of this product with stearyl alcohol yields a long-chain modified wax-like acetoacetate.

EXAMPLE 11

(a) 183 g (3 moles) of ethanolamine are slowly added to 1620 g (12 moles) of diethyl oxalate in 300 ml of ethanol at a maximum temperature of 0° C. The volatile constituents are then distilled off in vacuo. The residue is distilled in a high vacuum (b.p. 160° C./0.001 torr), affording 266 g (55% of theory) of oxalic acid ethyl ester (2-ethanolamide) in the form of a viscous oil. Transesterification of this compound with stearyl alcohol yields the corresponding stearyl derivative, from which the corresponding acetoacetate can be obtained by transesterification with ethyl acetoacetate.

(b) 80.6 g (0.5 mole) of the oxalic acid ethyl ester (2-ethanolamide) obtained in (a) are transesterified at 160° C. in 200 ml of ethyl acetoacetate. The volatile constituents are stripped off, leaving as residue a highly viscous oil, which immediately solidifies and is digested in diethyl ether. Yield: 85 g (70% of theory) of oxalic acid ethyl ester (2-ethanolamido-acetoacetate) in the form of a pale yellow powder with a melting point of 39°–40° C.

C₂H₅OCO—CONHC₂H₄OCOCH₂COCH₃ (stabiliser 11)

Transesterification of the above product with stearyl alcohol yields a long-chain modified wax-like product.

EXAMPLE 12

(a) 146.2 g (0.5 mole) of methyl β-(3,5-di-tert-butyl-4-hydroxy)propionate are reacted at 160° C. with 30.5 g (0.5 mole) of ethanolamine. The volatile constituents are stripped off, affording in quantitative yield an oil which immediately becomes a nacreous solid. Recrystallisation from toluene yields 148 g (92% of theory) of β-(3,5-di-tert-butyl-4-hydroxy)propionic acid (2-ethanolamide) with a melting point of 122°–123° C.

(b) 32.0 g (0.1 mole) of β-(3,5-di-tert-butyl-4-hydroxy)propionic acid (2-ethanolamide) are transesterified at 145° C. in 150 ml of methyl acetoacetate. The volatile constituents are stripped off, affording 40 g (98% of theory) of β-(3,5-di-tert-butyl-4-hydroxy)propionic acid (2-ethanolamido-acetoacetate) in the form of a highly viscous and almost colourless oil.

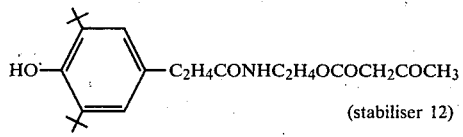

(stabiliser 12)

╋ = tert.-butyl

By procedures analogous to those described in the foregoing Examples 1–12 it is possible to obtain the following further stabilisers from the corresponding known stabilisers:
forming acid (2-ethanolamido-acetoacetate)
HCONHC₂H₄OCOCH₂COCH₃
trichloroacetic acid (2-ethanolamido-acetoacetate)
Cl₃COCONHC₂H₄OCOCH₂COCH₃
p-aminobenzoic acid (2-ethanolamido-acetoacetate)

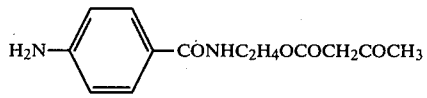

p-hydroxybenzoic acid (2-ethanolamido-acetoacetate)

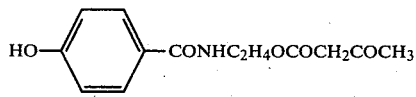

3,5-di-tert-butyl-4-hydroxybenzoic acid (2-ethanolamidoacetoacetate

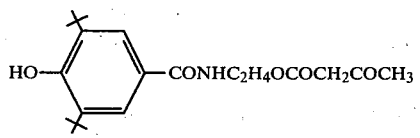

3-thia-4-(3,5-di-tert-butyl-4-hydroxy)butyric acid (2-ethanolamido-acetoacetate)

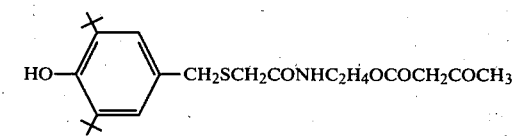

1-(acetoxyacetyloxy-2-ethyl)-3,4,5,6-tetrachlorophthalimide

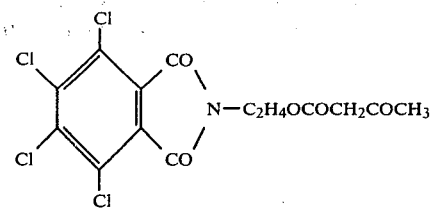

1-(acetoacetyloxy-2-ethyl)-3,4,5,6-tetrabromophthalimide

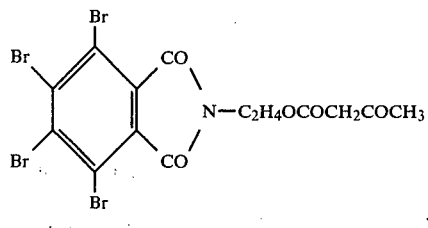

as well as compounds of the formulae
S(CH₂—CO—NHC₂H₄OCOCH₂COCH₃)₂
S(C₂H₄—CO—NHC₂H₄OCOCH₂COCH₃)₂

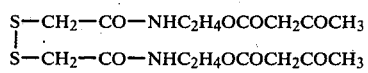

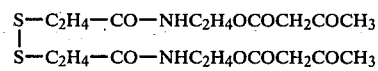

(C₂H₅O)₂POCH₂—CO—NHC₂H₄OCOCH₂COCH₃
(C₂H₅O)₂POC₂H₄—CO—NHC₂H₄OCOCH₂COCH₃
C₁₈H₃₇OCOCH=CHCO—NHC₂H₄OCOCH₂COCH₃

APPLICATION EXAMPLES

A dry blend consisting of 100 parts of S-PVC (K-value 58), 2 parts of epoxidised soybean oil, 0.9 part of calcium stearate, 0.6 part of zinc stearate and the amount of stabiliser indicated in Table 1 are rolled on a mixer roll for 5 minutes at 180° C. Samples having a thickness of 0.3 mm are taken from the rolled sheet obtained. The samples are subjected to heat in an oven at 180° C. and every 5 minutes the thermal ageing of a sample is determined according to the Yellowness Index (YI) of ASTM D 1925-70. The results are reported in Table 1.

TABLE 1

| Test | Stabiliser | Parts | Rolled sheet | Yellowness Index after 15 min. | 30 min. |
|---|---|---|---|---|---|
| 1 | — | — | 45.2 | 75.7 | 92.2 |
| 2 | stabiliser 5 | 0.8 | 11.2 | 20.1 | 51.7 |
| 3 | stabiliser 7 | 0.8 | 9.0 | 17.3 | 49.0 |
| 4 | stabiliser 8 | 0.8 | 7.2 | 10.8 | 18.9 |

This test was repeated in the same manner using 4 parts of epoxidised soybean oil, 0.4 part of calcium stearate, 0.2 part of zinc stearate and the indicated amount of Phosphite A (mixture of C₆H₅O—P(OC₁₄H₂₉)₂ and C₁₄H₂₉O—P(OC₆H₅)₂. The results are reported in Table 2.

TABLE 2

| Test | Stabiliser | Parts | Rolled sheet | Yellowness Index after 15 min. | 30 min. |
|---|---|---|---|---|---|
| 5 | stabiliser 5 | 0.6 | 6.7 | 12.6 | 33.0 |
|  | phosphite A | 0.3 |  |  |  |
| 6 | stabiliser 5 | 0.6 | 6.0 | 13.0 | 21.5 |
|  | phosphite A | 0.6 |  |  |  |

What is claimed is:

1. A compound of the formula

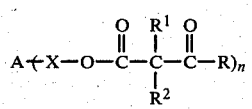
(I)

wherein n is an integer from 1 to 2, R is $C_1$–$C_{24}$ alkyl or phenyl, each of $R^1$ and $R^2$ independently is hydrogen or R, and X is $C_1$–$C_6$ alkylene or $C_2$–$C_6$ alkylene having oxygen between any two adjacent carbon atoms and, if n is 1, A is

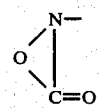
(II)

wherein Q is a group of —Z—CO, wherein the carbonyl group is attached to the nitrogen of the formula II, and Z is o-phenylene which can be substituted by a group —CON($R^6$)$R^7$, —COO$R^8$ or —COS$R^8$, or by 4 halogen atoms, $R^6$ and $R^7$ are the same or different and are hydrogen or $C_1$–$C_{12}$-alkyl and $R^8$ is $C_1$–$C_{12}$ alkyl, and, if n is 2, A is one of the groups of the formulae

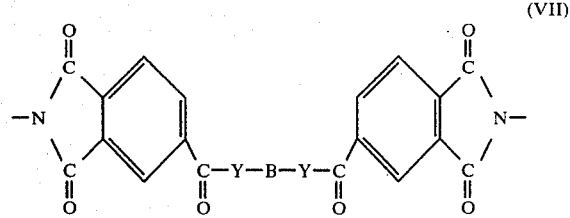
(VII)

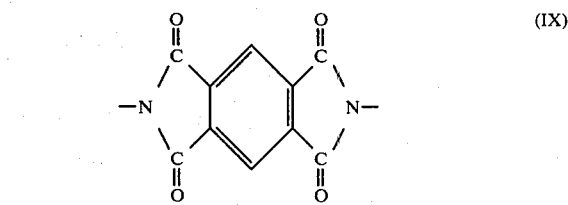
(IX)

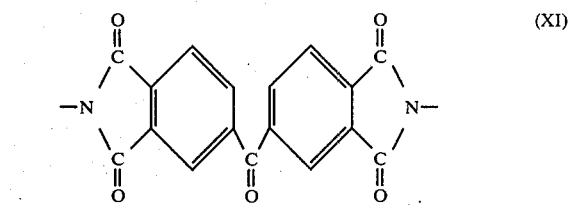
(XI)

wherein Y can be —O— or —NH—, B is $C_1$–$C_6$ alkylene, p-phenylene or one of the groups [$-$($CH_2$)$_q$O$]_r$($-$C$H_2$)$_q$ or $-$[($CH_2$)$_q$S$]_r$($CH_2$)$_q$, wherein q is an integer from 1 to 4 and r is an integer from 1 to 3.

2. A compound according to claim 1 of the formula I, wherein n is 1 or 2, R is methyl or phenyl, $R^1$ and $R^2$ are hydrogen, and X is $C_2$–$C_3$ alkylene or a group —$CH_2CH_2O$—$CH_2CH_2$, and if n is 2, A is one of the groups of the formulae IX or XI.

3. A compound according to claim 1 of the formula I, wherein R is methyl and X is $C_2$–$C_3$ alkylene, n is 1 or 2, and, if n is 1, A is a group of the formula

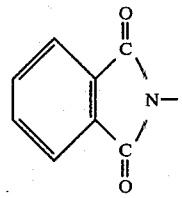

and, if n is 2, A is one of the groups of the formulae IX or XI.

* * * * *